(12) United States Patent
Vitt et al.

(10) Patent No.: US 7,236,827 B2
(45) Date of Patent: Jun. 26, 2007

(54) SINGLE-USE MEDICAL DEVICE

(75) Inventors: Elmar Vitt, Hamburg Rotherbaum (DE); Gregor Niewalda, Erlangen (DE); Max Schaldach, deceased, late of Erlangen (DE); by Max Schaldach, Jr., legal representative, Berlin (DE)

(73) Assignee: Biotronik Mess- und Therapiegeraete GmbH & Co. Ingenieurbuero Berlin, Berlin (DE)

( * ) Notice: Subject to any disclaimer, the term of this patent is extended or adjusted under 35 U.S.C. 154(b) by 632 days.

(21) Appl. No.: 10/200,567

(22) Filed: Jul. 19, 2002

(65) Prior Publication Data

US 2003/0045903 A1 Mar. 6, 2003

(30) Foreign Application Priority Data

Jul. 20, 2001 (DE) ................. 101 36 642

(51) Int. Cl.
*A61N 1/00* (2006.01)
(52) U.S. Cl. .......................... 607/27; 607/63
(58) Field of Classification Search ................ 607/62, 607/63, 27, 37, 38
See application file for complete search history.

(56) References Cited

U.S. PATENT DOCUMENTS

| | | | | | |
|---|---|---|---|---|---|
| 4,026,305 | A | * | 5/1977 | Brownlee et al. | 607/32 |
| 4,164,946 | A | * | 8/1979 | Langer | 607/27 |
| 5,050,600 | A | * | 9/1991 | Parks | 607/10 |
| 5,350,407 | A | | 9/1994 | McClure | |
| 5,476,485 | A | * | 12/1995 | Weinberg et al. | 607/28 |
| 5,486,200 | A | | 1/1996 | Lindemans | |
| 5,522,856 | A | | 6/1996 | Reineman | |
| 5,522,897 | A | | 6/1996 | King | |
| 5,591,217 | A | | 1/1997 | Barreras | |
| 5,662,694 | A | | 9/1997 | Lidman | |
| 5,925,069 | A | | 7/1999 | Graves | |
| 5,944,745 | A | | 8/1999 | Rueter | |
| 6,009,878 | A | * | 1/2000 | Weijand et al. | 128/899 |
| 6,070,099 | A | * | 5/2000 | Magin | 607/5 |
| 6,132,086 | A | | 10/2000 | Henwood | |
| 6,158,314 | A | * | 12/2000 | Thead et al. | 83/23 |
| 6,230,058 | B1 | | 5/2001 | Legay | |
| 6,880,085 | B1 | * | 4/2005 | Balczewski et al. | 713/182 |
| 6,917,831 | B2 | * | 7/2005 | Bloemer et al. | 607/16 |
| 2002/0068956 | A1 | | 6/2002 | Bloemer | |

FOREIGN PATENT DOCUMENTS

| | | |
|---|---|---|
| DE | 199 03 385 A1 | 8/2000 |
| DE | 1 192 972 A2 | 4/2002 |
| EP | 0 572 799 A1 | 12/1993 |
| GB | 2 336 214 A | 10/1999 |
| WO | WO 01/35813 A1 | 5/2001 |

* cited by examiner

*Primary Examiner*—Scott M. Getzow
(74) *Attorney, Agent, or Firm*—Hahn Loeser & Parks, LLP

(57) ABSTRACT

An electrical therapy device has a blocking triggering unit and a re-use blocking unit. The re-use blocking unit prevents the functions of the electrical therapy device during implantation in dependence on the condition of the blocking triggering unit. The blocking triggering unit is triggered either upon implantation or explantation of the electrical therapy device. In some aspects, an electrical therapy device has a blocking triggering unit and a re-use blocking unit, wherein the re-use blocking unit prevents the functions of the electrical therapy device in dependence on the condition of the blocking triggering unit. The blocking triggering unit is triggered upon explantation of the electrical therapy device.

36 Claims, 3 Drawing Sheets

SINGLE-USE MEDICAL DEVICE

The present invention concerns an electrical therapy device for implantation in a body, an electrical therapy device together with an associated packaging, a packaging for an electrical therapy device, and a medical implant with a housing.

BACKGROUND OF THE ART

From a purely technical point of view some single-use medical implants such as for example cardiac pacemakers, defibrillators or electrodes can in principle also be re-used or put to further use after explantation of those implants out of a patient. Explanation of implants is effected for example upon a change in medical indication or after the decease of a patient.

It happens that implants of that kind are restored again after explantation. For that purpose the implant is cleaned, disinfected and sterilised. Such re-use is generally effected without the knowledge of the patient and without approval from the manufacturer.

In regard to the development and manufacture of medical products for one-time use, it will be appreciated that there are numerous aspects to be taken into account, which can influence the safety and efficiency of such products. Those aspects include for example previous germ contamination of the product, the behaviour of the material in regard to use, compatibility of product, packaging and sterilisation process, durability period of the materials and durability period of the sealing seams of the sterile packaging. In contrast to a manufacturer, restorers frequently do not have those important items of information.

After use of the implant and subsequent restoration by cleaning, disinfecting and sterilisation, those medical products may suffer from deficiencies. Such deficiencies may involve inter alia the existence of microcracks, inadequate freedom from germs, inadequate freedom from pyrogens, the presence of particles and endotoxins, an impairment in material properties, consumption of the batteries, the loss of electrical safety and the occurrence of dangerous substances due to cleaning and re-sterilisation.

Therefore, in spite of implants of that kind having been reprocessed, the re-use thereof still entails some dangers. It is not possible to exclude the functional capability being adversely affected or a reduction in the remaining operational service life by virtue of the period of use which has already elapsed or patient infection. The risks which occur as a result of this are on the one hand ethically unjustifiable and on the other hand they can give rise to product liability problems.

Therefore the object of the present invention is to provide electrical therapy devices and medical implants which can prevent unauthorised re-use.

SUMMARY OF THE INVENTION

The object of the invention is attained by an electrical therapy device having the features of accompanying claim 1.

In that respect the invention is based on the idea of providing an electrical therapy device which has a blocking triggering unit and a re-use blocking unit, wherein the re-use blocking unit prevents the functions of the electrical therapy device during implantation in dependence on the condition of the blocking triggering unit. The blocking triggering unit is triggered either upon implantation or explantation of the electrical therapy device.

The advantages that the invention entails are in particular that the re-use blocking unit upon implantation into a body interrogates the condition of the blocking triggering unit and on the basis of that condition can establish whether the electrical therapy device has already been previously implanted once. If the condition of the blocking triggering unit indicates that the electrical therapy device has already been implanted once the re-use blocking unit interrupts the functions of the electrical therapy device. In other words the electrical therapy device cannot be implanted a second time and thus re-used. The condition of the blocking triggering unit, upon implantation or explantation, is altered in such a way that it is possible for the re-use blocking unit to detect that the electrical therapy device has already been used previously.

The above-mentioned alternative configuration also includes for example a cardiac pacemaker in which a component is destroyed or altered, with the connection of an electrode line, in which case then the cardiac pacemaker only remains still operational with the electrode line connected. In that case the re-use block is initialised with the connection of the electrode line. The re-use block is then triggered with subsequent disconnection of the electrode line from the cardiac pacemaker and the function of the cardiac pacemaker or defibrillator is permanently prevented. That can be effected for example by the change in or destruction of the corresponding component with connection of the electrode line resulting in a further change in or destruction of a component of the implant, upon subsequent disconnection of the electrode line.

In this embodiment therefore rendering the electrical therapy device unusable firstly presupposes initial initialisation of the re-use block and later triggering of the re-use block. The re-use block therefore firstly has to be made live before it can be triggered. Both initialisation of the electrical therapy device upon implantation and also triggering of the re-use block or the re-use block being in a triggered condition are detected so that the functions of the electrical therapy device are prevented. In other words, prevention of the functions of the electrical therapy device occurs upon or in the course of implantation of the electrical therapy device.

The object of the invention is further attained by an electrical therapy device having the features of accompanying claim 2.

In this respect the invention is based on the consideration of providing an electrical therapy device which has a blocking triggering unit and a re-use blocking unit, wherein the re-use blocking unit prevents the functions of the electrical therapy device in dependence on the condition of the blocking triggering unit. The blocking triggering unit is triggered upon explantation of the electrical therapy device.

In that respect it has proven to be advantageous that the condition of the blocking triggering unit is set, upon explantation of the electrical therapy device, in such a way that the re-use blocking unit can detect that explantation of the electrical therapy device has occurred. The re-use blocking unit can immediately prevent the functions of the electrical therapy device as soon as it has detected, on the basis of the condition of the blocking triggering unit, that the therapy device is no longer in the body, that is to say explantation has occurred. In this variant of the invention the functions of the electrical therapy devices can be interrupted immediately after detection of explantation while an interruption in the functions of the electrical therapy device in the case of the variant set forth in claim 1 occurs only upon fresh implantation of the electrical therapy device in a body.

The above-mentioned alternative configuration also includes for example a cardiac pacemaker which, upon being brought into operation, after the connection of an electrode line, is irrevocably put into a condition which directly results in the cardiac pacemaker being unusable after the electrode line is disconnected for the first time from the cardiac pacemaker.

In this alternative configuration it is only necessary to detect disconnection of the electrode line from the cardiac pacemaker to directly trigger off a block. There is no need for a preceding initialisation step.

In an embodiment of the invention the electrical therapy device further has an energy supply unit which supplies the therapy device with the necessary energy. In that case the re-use blocking unit has a triggering device which is suitable for disconnecting the energy supply unit from the remaining units of the electrical therapy device, in dependence on the condition of the blocking triggering unit, in order thereby to interrupt the supply of energy to the therapy device.

Disconnection of the energy supply unit from the remaining units or at least essential units of the electrical therapy device ensures that the electrical therapy device can no longer be put to further use as it is no longer supplied with energy.

In a further embodiment of the invention the re-use blocking unit triggers the blocking triggering unit upon disconnection of an electrode line from the electrical therapy device. In that respect separation of the electrode line from the electrical therapy device is used as an indication that the electrical therapy device has been explanted and is not ever to be used again.

In a further embodiment of the invention the electrical therapy device has a control means which controls the general functions of the therapy device. In that arrangement the re-use blocking unit is suitable for at least partially blocking or preventing the electrical control of the therapy device by instructions to the control means during implantation of the electrical therapy device in dependence on the condition of the blocking triggering unit. Therefore the condition of the blocking triggering unit is interrogated. If that condition indicates return to operation, the function of the implant is prevented by the control means. That permits electrical or electronic blocking of the electrical therapy device so that it cannot be put to further use as it has already been implanted into a body once.

The blocking triggering unit can be so designed that the condition thereof is altered with a one-off inquiry so that upon a second inquiry it is in a second condition which indicates that the blocking triggering unit has already been the subject of inquiry previously and thus unwanted re-use is being attempted. The conditions of the blocking triggering unit can be represented for example by a single bit in a memory, which is set in the manner of a flag upon first response in respect of the memory and which can then be reset either not at all or only under particular conditions. A suitable memory would be for example an EPROM.

In still a further embodiment of the invention the re-use blocking unit has a first receiving unit. In that respect the first receiving unit represents either a telemetric receiving unit or a magnetically activatable receiving unit. In that respect a telemetric receiving unit is suitable, upon reception of a telemetric blocking signal, to activate or trigger the blocking triggering unit. In contrast a magnetically activatable receiving unit is suitable for activating or triggering the blocking triggering unit upon magnetic activation of the receiving unit.

In that way the blocking triggering unit can be activated from a position outside the body in a contact-less manner—telemetrically or magnetically—in order to prevent the therapy device from being implanted into a body again after explantation. That contact-less activation of the blocking triggering unit can be executed for example in the course of first implantation.

In a further configuration of the invention the control means has a memory for a patient-specific works operating program for operation of the electrical therapy devices. The re-use blocking unit further has an initialisation detection unit which is adapted to activate or trigger the blocking triggering unit upon initialisation of the works operating program which is stored in the memory of the control means.

In a further embodiment of the invention the re-use blocking unit has an impedance measuring unit which determines the impedance of an electrode line connected to the electrical therapy devices and triggers or activates the blocking triggering unit when the measured impedance of the electrode line deviates from a predetermined value or range of values.

Thus it is possible on the part of the re-use blocking unit to establish when the electrode line is removed from the electrical therapy device. On the basis of that detection effect the blocking triggering unit is activated and the electrical therapy device is blocked immediately or at latest upon a subsequent implantation procedure so that it can no longer be put to further use.

In a further configuration of the invention the electrical therapy device has a blocking deactivation means which is adapted to overwrite the condition of the blocking triggering unit upon the reception of a blocking deactivation signal. The condition of the blocking triggering unit can be altered by way of the blocking deactivation means so that authorised re-use or processing is possible.

In a further embodiment of the invention the blocking deactivation means has a telemetric receiving unit which is adapted to telemetrically receive the blocking deactivation signal. In that way it is possible for the re-use block of the electrical therapy device to be deactivated in a contact-less mode.

In a further embodiment of the invention the blocking deactivation means has a decoding means which is suitable for decoding an encoded password from a received signal. The blocking deactivation means further has a verification means which is adapted to verify the received decoded password and to reset the condition of the blocking triggering unit when the received password is correct.

The use of a password ensures that only authorised persons are in a position to again deactivate the activated condition of the blocking triggering unit.

In a further embodiment of the invention the re-use blocking unit has a detection unit which is adapted to monitor ECG signals from the heart and to activate the blocking triggering unit as soon as no more ECG signals are received in a predetermined period of time. It is possible in that way to detect that the electrical therapy device is no longer in a body and therefore has to be blocked.

In a further embodiment of the invention the electrical therapy device has a temperature sensor which detects the temperature in the electrical therapy device and transmits it to the re-use blocking unit. The re-use blocking unit also has a temperature evaluation unit which is suitable for activating the blocking triggering unit when the temperature outputted by the temperature sensor in the electrical therapy device falls below a predetermined threshold value. In that way it is possible to establish on the basis of temperature whether the electrical therapy device is still in the body. If that is not the case the temperature in the electrical therapy device will fall below a predetermined value so that the blocking triggering unit is activated.

The object of the invention is attained by an electrical therapy device as described hereinbefore and an associated packaging as set forth in claim 15.

In that respect the invention is based on the idea of providing an electrical therapy device together with associated packaging. In that case the packaging has a magnet arranged in the packaging in such a way that a magnetically activatable receiving unit in the re-use blocking unit is magnetically activated upon removal of the electrical therapy device from the packaging and thus the blocking triggering unit is triggered. Therefore the re-use block is activated upon removal of the electrical therapy device from the packaging.

The object of the invention is further attained by a packaging for an electrical therapy device as set forth in claim 16.

In that respect the basic starting point is the idea that the packaging includes a magnet which is arranged in such a way that the magnetically activatable receiving unit is magnetically activated upon removal of the electrical therapy device from the packaging and the blocking triggering unit is thus activated or triggered.

The object of the invention is also attained by a medical implant having a housing and the features as set forth in claim 17.

In that respect the invention is based on the idea of providing the housing of a medical implant at least in a portion-wise manner with a biocompatible layer which reacts chemically upon contact with human tissue. The result of that chemical reaction is visible in that case. On the basis of the visible result it is possible to establish whether that medical implant has already been implanted into a body once so that it may not be used again.

Alternative ways of attaining the object provide on the one hand, in the case of an implant which is not necessarily electrical, providing components which externally recognisably change in the course of implantation or as a consequence of being implanted. That can be a mechanically triggered display or indication, for example an indication which does not readily reversibly change over upon the connection of an electrode line to a cardiac pacemaker so that this indication clearly indicates to a doctor carrying out an implantation procedure whether the corresponding pacemaker has already been used, that is to say connected to an electrode line, or not.

The component may also be a chemical one which, as a consequence of coming into contact with the body chemistry of a patient, after implantation, irreversibly externally recognisably changes, for example in terms of color. Such a component may also be provided in the case of a purely mechanical implant such as for example a catheter. It may also be only partially provided, in particular in such a way that coloration of the component causes the appearance of script such as 'This catheter has already been used and is not suitable for use again'.

Further possible mechanical re-use blocks for electrical or mechanical implants or medical devices can be for example single-use retaining or latching connections. For example, for connecting an electrode line to a cardiac pacemaker it is possible to provide, either at the pacemaker side or at the electrode side, barbs which irretrievably destroy the connection, preferably in regard to the pacemaker, insofar as the connection on the pacemaker side is mechanically destroyed or non-removable remains of a necessary connecting portion between the electrode line and the pacemaker remain in the connection on the pacemaker side so that it is no longer possible for an electrode line to be connected to the pacemaker.

BRIEF DESCRIPTION OF THE DRAWINGS

The invention is described in greater detail hereinafter by means of embodiments with reference to the drawings in which.

DETAILED DESCRIPTION OF A PREFERRED EMBODIMENT

Figure 1:
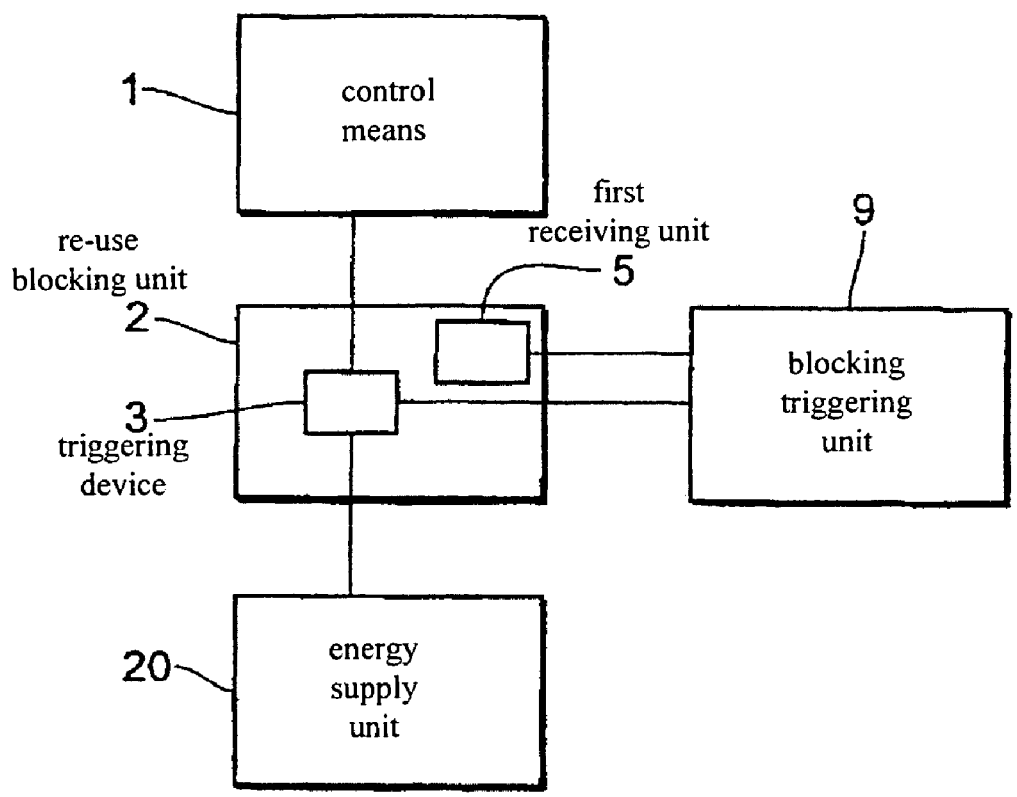
FIG. 1 shows a block circuit diagram of an electrical therapy device in accordance with a first embodiment of the invention.

FIG. 1 shows a block circuit diagram of an electrical therapy device in accordance with a first embodiment. The electrical therapy device has a control means 1, a blocking triggering unit 9, a re-use blocking unit 2 and an energy supply unit 20. The re-use blocking unit 2 is respectively connected to the control means 1, the blocking triggering unit 9 and the energy supply unit 20. The re-use blocking unit 2 has a triggering device 3 and a first receiving unit 5. The triggering device 3 is connected to the control means 1, the energy supply unit 20 and the blocking triggering unit 9. The first receiving unit 5 is connected to the blocking triggering unit 9.

The first receiving unit 5 is a wirelessly activatable receiving unit such as for example a telemetric receiving unit or a magnetically activatable receiving unit. The first receiving unit 5 can be activated for example by a telemetric signal (in the case of a telemetric receiving unit) or by a magnet (in the case of a magnetically activatable receiving unit). When the first receiving unit 5 receives a corresponding telemetric or magnetic signal it activates the blocking triggering unit 9. The triggering device 3 is disposed between the control means 1 and the energy supply unit 20 and can be used to separate the energy supply unit 20 from the rest of the electrical therapy device.

Upon initialisation of the therapy device during implantation thereof in a body the re-use blocking unit 2 checks the condition of the blocking triggering unit 9. If the blocking triggering unit 9 is activated at that time that is transmitted to the triggering device 3 which is then activated and the connection between the energy supply unit 20 and the control means 1 is interrupted. The control unit 1 is therefore no longer supplied with energy and is consequently switched off. The electrical therapy device can thus not be further used.

The condition of the blocking triggering unit 9 serves as an indicator as to whether the electrical therapy device has already been previously implanted in a body. In the case of authorised implantation the blocking triggering unit 9, after successful implantation of the electrical therapy device, is activated by means of the first receiving unit 5. That can be effected telemetrically or by magnetic activation of the receiving unit.

Figure 2:
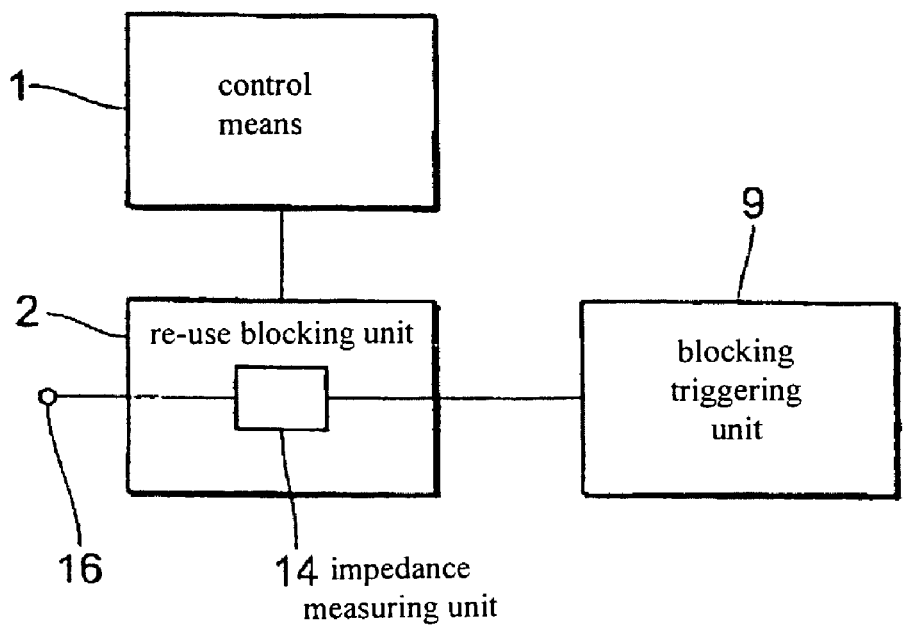
FIG. 2 shows a block circuit diagram of an electrical therapy device in accordance with a second embodiment of the invention.

FIG. 2 shows a block circuit diagram of an electrical therapy device in accordance with the second embodiment. In this arrangement the therapy device has a control means 1, a re-use blocking unit 2 and a blocking triggering unit 9. The electrical therapy device also has a connection 16 for an electrode line. The re-use blocking unit 2 is respectively connected to the control means 1, the blocking triggering unit 9 and the connection 16 and has an impedance measuring unit 14. In this case the impedance measuring unit 14 is connected to the connection 16 for the electrode line and to the blocking triggering unit 9.

The impedance measuring unit 14 detects the impedance at the connection 16 and thus the impedance of a connected electrode line. That detection operation can be effected continuously or at discrete intervals of time. In the impedance measuring unit 14, the measured impedance values are compared to a previously inputted threshold value or range of threshold values. If the measured impedance values in that case deviate from that range of threshold values the impedance measuring unit 14 activates the blocking triggering unit 9. In that case the previously inputted threshold values or ranges of threshold values are so selected that a deviation from those values can only occur if the electrode line is removed from the connection 16, that is to say if the electrode line is disconnected. Measurement of the impedance at the connection 16 affords a reliable indicator as to whether electrode lines are or are not still connected to the electrical therapy device. If the electrode lines are no longer connected to the electrical therapy device this can mean that the electrical therapy device has been removed from the body.

Upon initialisation of the therapy device during implantation thereof in a body the re-use blocking unit 2 checks the condition of the blocking triggering unit 9. If the blocking triggering unit 9 is activated at that time the re-use blocking unit 2 gives an instruction to the control means 1 to block control of the functions of the electrical therapy device. As an alternative thereto the energy supply to the control means can be blocked, as described in the first embodiment in relation to FIG. 1. In both cases, the consequence of this is that the electrical therapy device cannot be further used.

As an alternative thereto the re-use blocking unit 2 can for example immediately interrupt the energy supply as soon as the measured impedance values deviate excessively from the range of threshold values, that is to say the electrode line has been removed.

Figure 3:
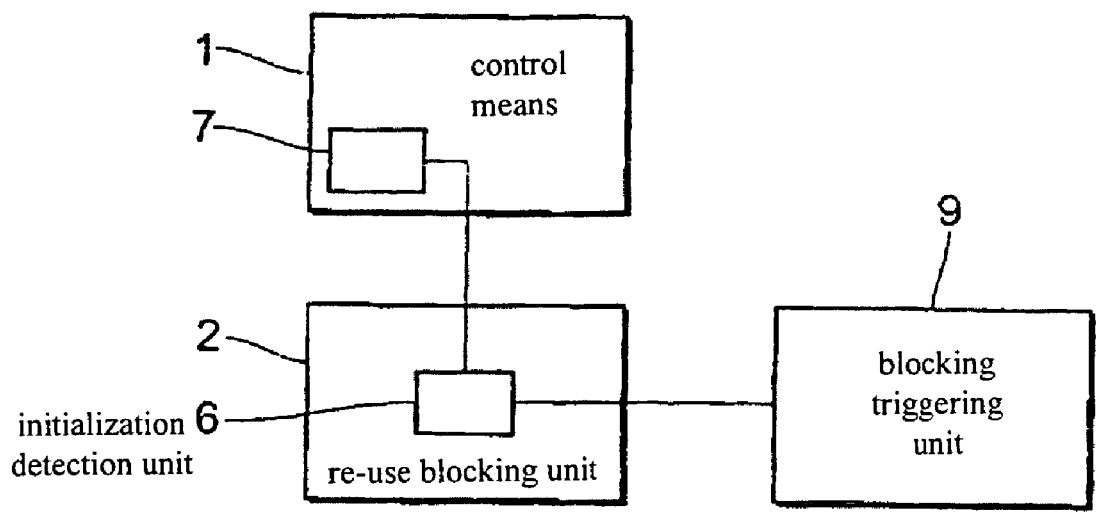
FIG. 3 shows a block circuit diagram of an electrical therapy device in accordance with a third embodiment of the invention.

FIG. 3 shows a block circuit diagram of an electrical therapy device in accordance with a third embodiment. The electrical therapy device in this case has a control means 1, a re-use blocking unit 2 and a blocking triggering unit 9. The re-use blocking unit 2 in this arrangement is respectively connected to the control means 1 and the blocking triggering unit 9. The control means 1 has a memory 7 for the storage of a works operating program. The re-use blocking unit 2 has an initialisation detection unit 6 connected to the blocking triggering unit 9 and the memory 7.

The initialisation detection unit 6 detects initialisation of the works operating program in the memory 7 for control of the electrical therapy device in accordance with the patient-specific parameters during implantation of the electrical therapy device in a body. When such initialisation of the works operating program has been detected the initialisation detection unit 6 activates the blocking triggering unit 9.

Upon each initialisation for implantation of the electrical therapy device the re-use blocking unit 2 checks the condition of the blocking triggering unit 9. If the blocking triggering unit 9 is activated the control of the electrical therapy device is blocked. The details of that blocking action are already described in the first and second embodiments with reference to FIGS. 1 and 2.

Figure 4:
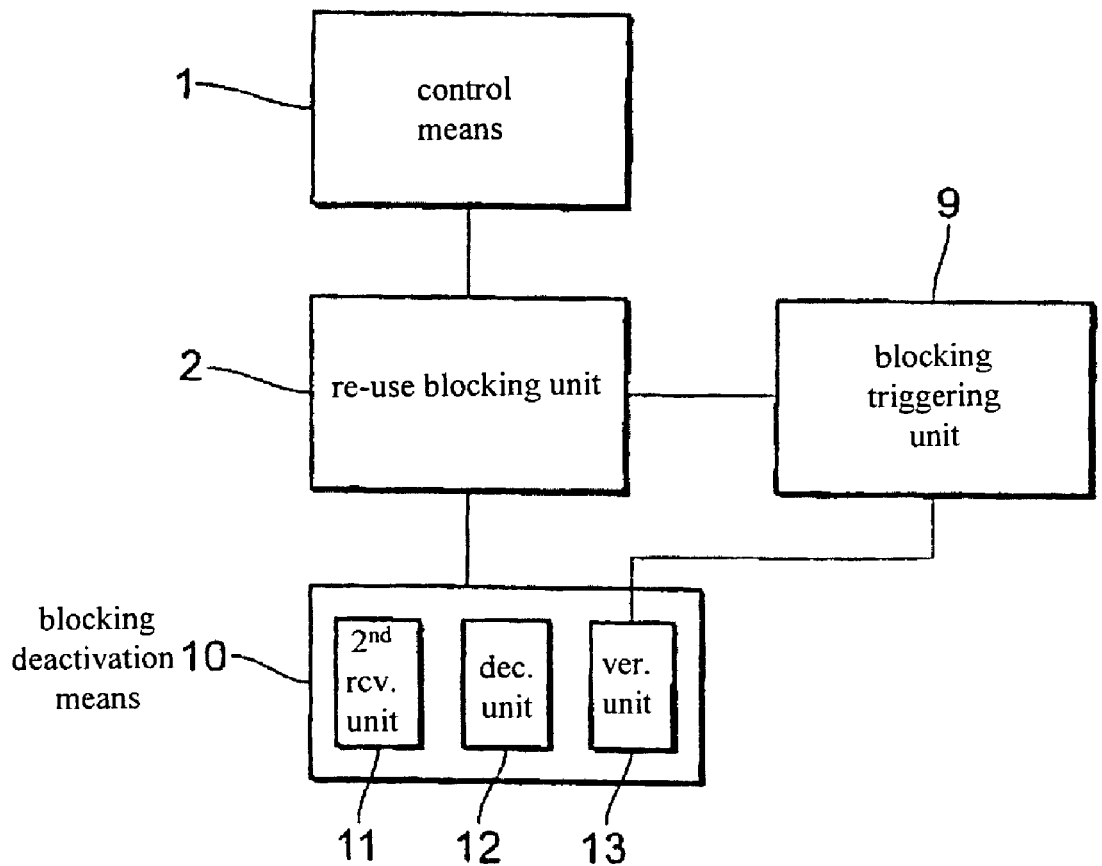
FIG. 4 shows a block circuit diagram of an electrical therapy device in accordance with a fourth embodiment of the invention.

FIG. 4 shows a block diagram of an electrical therapy device in accordance with a fourth embodiment of the invention. In this case the electrical therapy device has a control means 1, a re-use blocking unit 2, a blocking triggering unit 9 and a blocking deactivation means 10. The re-use blocking unit 2 is respectively connected to the control means 1, the blocking triggering unit 9 and the blocking deactivation means 10. The blocking deactivation means 10 has a second receiving unit 11, a decoding unit 12 and a verification unit 13 which are arranged in succession in that sequence. The receiving unit 11 is for example a telemetric receiving unit as has already been described in the first embodiment.

The second receiving unit 11 receives a telemetric signal by which data and instructions are transmitted. The received telemetric signal is decoded in the decoding unit 12 so that the data, instructions and information contained in the telemetric signal are extracted. The verification unit 13 checks those decoded items of information with a predetermined password. If the decoded items of information or data correspond to that predetermined password the verification unit 13 deactivates the blocking triggering unit 9, that is to say the condition of the blocking triggering unit 9 is reset. The use of a password and verification of that password in the verification unit 13 ensures that the re-use block in the blocking triggering unit 9 can only be reset by authorised persons. By removal of the re-use block in the blocking triggering unit 9, it is possible to provide that the electrical therapy device is not deactivated upon implantation, although such implantation possibly already represents the second implantation.

Figure 5:
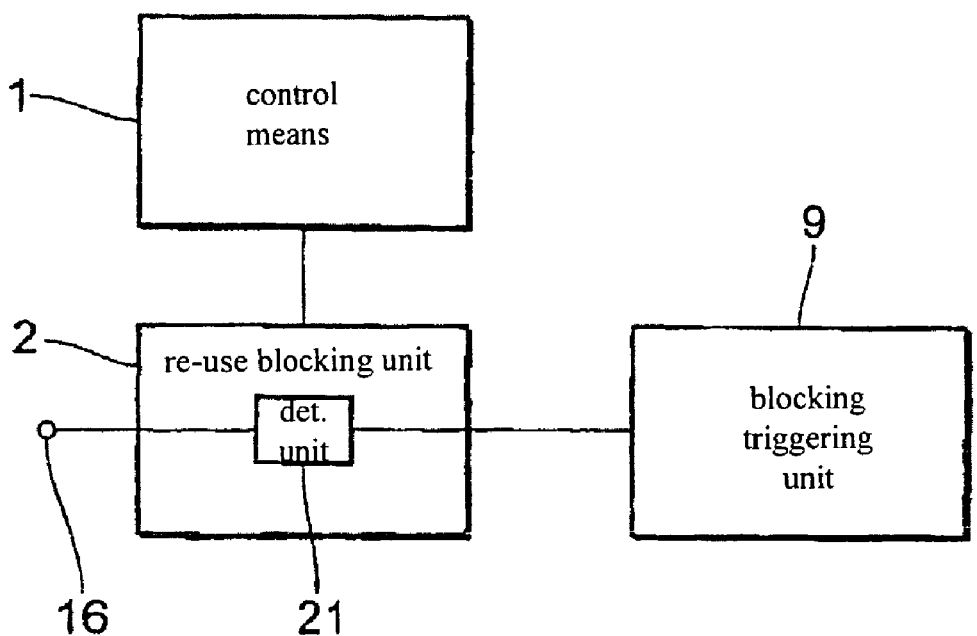
FIG. 5 shows a block circuit diagram of an electrical therapy device in accordance with a fifth embodiment of the invention.

FIG. 5 shows a block circuit diagram of an electrical therapy device in accordance with the fifth embodiment of the invention. The electrical therapy device has a control means 1, a re-use blocking unit 2 and a blocking triggering unit 9 as well as a connection 16 for the connection of an electrode line. The re-use blocking unit 2 is respectively connected to the control means 1, the connection 16 and the blocking triggering unit 9 and has a detection unit 21. The detection unit 21 is connected to the connection 16 and the blocking triggering unit 9.

The ECG signals of the heart of a patient are transmitted to the detection unit 21 by way of an electrode line connected to the connection 16. There, the ECG signals are detected continuously or at predetermined moments in time. As soon as no ECG signals are received in a predetermined period of time the detection unit 21 activates the blocking triggering unit 9, that is to say the re-use block is set. In that respect the absence of ECG signals is used as an indicator that the electrode line has been separated from the electrical therapy device, and therefore the electrical therapy device is no longer in the body of the patient and explantation of the therapy device has occurred.

The re-use blocking unit 2 can block or interrupt the functions of the electrical therapy device on the one hand immediately after activation of the blocking triggering unit 9 or however only upon subsequent implantation. Further details in that respect have already been described hereinbefore with reference to the first and second embodiments.

Figure 6:
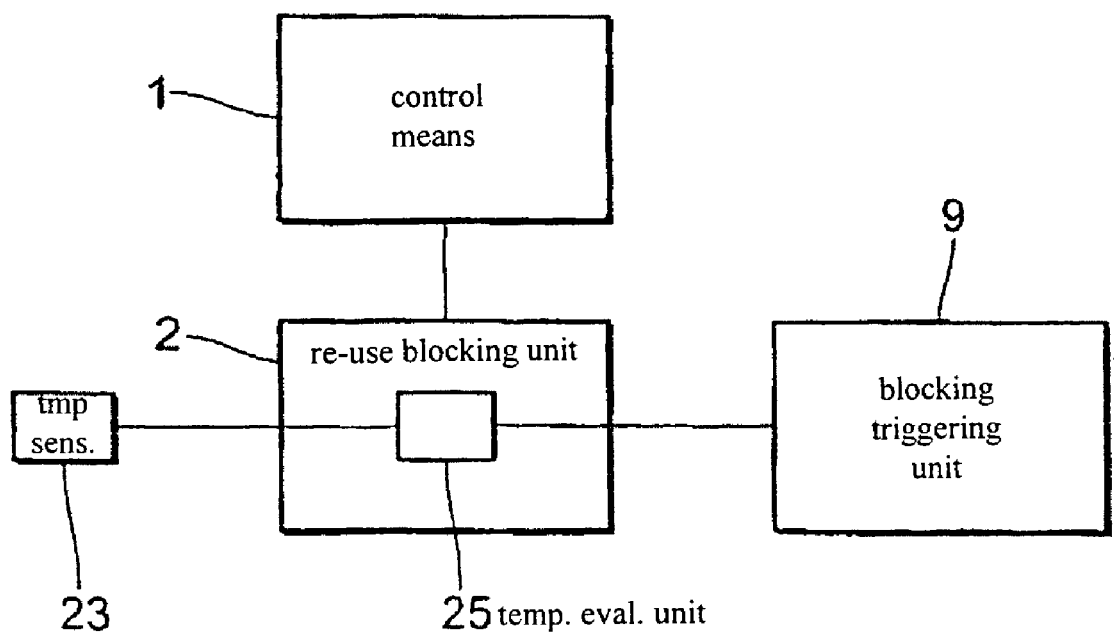
FIG. 6 shows a block circuit diagram of an electrical therapy device in accordance with a sixth embodiment of the invention.

FIG. 6 shows a block circuit diagram of an electrical therapy device in accordance with a sixth embodiment. In this case the electrical therapy device has a control means 1, a re-use blocking unit 2, a blocking triggering unit 9 and a temperature sensor 23. The re-use blocking unit 2 is respectively connected to the control means 1, the blocking triggering unit 9 and the temperature sensor 23 and has a temperature evaluation unit 25. In this case the temperature evaluation unit 25 is connected to the temperature sensor 23 and the blocking triggering unit 9.

The temperature sensor 23 detects the temperature in the electrical therapy device. This can take place both continuously and also at fixed intervals of time. The temperature sensor 23 transmits the detected temperature to the temperature evaluation unit 25 where the detected temperature is compared to a predetermined threshold value. If the detected temperature falls below the predetermined threshold value the temperature evaluation unit 25 activates the blocking triggering unit 9, that is to say the re-use block is activated. The temperature in the electrical therapy device is used in that case as an indicator as to whether the electrical therapy device is still in a body or whether explantation of the electrical therapy device has taken place.

The re-use blocking unit 2 can block or interrupt the functions of the electrical therapy device on the one hand immediately after activation of the blocking triggering unit 9 or however only upon subsequent implantation. Further details in that respect have already been described hereinbefore with reference to the first and second embodiments.

The blocking triggering unit 9 can represent for example a non-volatile and non-erasable memory in which for example a flag is set for activation purposes. Such a memory can represent for example an EPROM. The re-use block is thus activated when that flag is set.

The memory 7 in the control means 1 can for example have a memory in which patient-specific parameters are stored. That memory could represent for example an EPROM, that is to say the parameters stored in that memory can no longer be subsequently altered. This would mean that the electrical therapy device can only be used for a single medical indication for a specific patient.

The blocking triggering unit 9 could be embodied for example by an electronic switch such as a transistor, a fuse or a relay.

The triggering device 3 could also be embodied for example by an electronic switch such as a transistor, a fuse or a relay.

Preferably, both for the blocking triggering unit 9 and also for the triggering device 3, use is made of a fuse which can burn through for activation so that the blocking triggering unit and the triggering device can no longer be activated after activation thereof. That would ensure that the electrical therapy device cannot be re-used or processed without proper authority.

The term electrical therapy device is used here to denote for example cardiac pacemakers, defibrillators or the like.

In an alternative embodiment of the invention the connection 16 for an electrode line is designed in such a way that a portion of the connection 16 is broken through or ruptured upon insertion of the plug of the electrode line. In the inserted condition the plug of the electrode line represents a means for bridging over the ruptured portion of the connection 16 so that there is still an electrical communication. If however the plug of the electrode line is pulled out the bridging across the ruptured portion is removed and there is thus no longer an electrical communication. The absence of an electrical contact or communication in the connection 16 after the plug of the electrode line has been pulled out can be used to provide that the energy supply to the electrical therapy device is interrupted and the electrical therapy device is no longer operational.

In a further alternative embodiment of the invention there is provided a medical implant having a housing. In that case the housing of the medical implant is coated at least in a portion-wise manner with a biocompatible layer. In that respect the biocompatible layer is such that it reacts chemically upon contact with human tissue. The result of that chemical reaction is visible in that case to the human eye.

This therefore provides that it is possible to see when a medical implant has already been previously implanted in a body. The doctor carrying out the treatment is then in a position to refuse that medical implant and instead thereof to obtain a fresh implant directly from the manufacturer.

A further alternative embodiment of the invention represents a packaging for an electrical therapy device for example in accordance with the first embodiment. In this case a magnet is disposed in or on the packaging in such a way that the first magnetic activatable receiving unit 5 is activated when the electrical therapy device is removed from the packaging. As described in the first embodiment activation of the first receiving unit 5 provides that the blocking triggering unit 9 and thus the re-use block is activated.

The invention claimed is:

1. An electrical therapy device for implantation in a body, wherein the electrical therapy device is a pacemaker or a defibrillator capable of being connected to an electrode line upon implantation into said body, said electrical therapy device comprising:
   a blocking triggering unit adapted to be triggered upon separation of said electrode line from the electrical therapy device, indicating explantation of the electrical therapy device from said body; and
   a re-use blocking unit adapted to prevent functions of the therapy device in dependence on a condition of the blocking triggering unit, including a condition of said blocking triggering unit indicating a triggering of said blocking triggering unit in response to said separation of said electrode line from said electrical therapy device.

2. The electrical therapy device according to claim 1, wherein the re-use blocking unit is further adapted to prevent said functions of the therapy device in dependence on said condition of the blocking triggering unit during implantation of the therapy device.

3. The electrical therapy device of claim 2, wherein:
   the re-use blocking unit triggers the blocking triggering unit upon separation of the electrode line from the electrical therapy device.

4. The electrical therapy device of claim 2, wherein:
   the re-use blocking unit comprises an impedance measuring unit for determining an impedance of the electrode line and for triggering the blocking triggering unit if the measured impedance deviates from a predetermined value.

5. The electrical therapy device of claim 2, wherein:
   the re-use blocking unit comprises a detection unit for monitoring ECG signals of the heart and to trigger the blocking triggering unit when no more ECG signals are received in a predetermined period of time.

6. The electrical therapy device of claim 2, further comprising:
a temperature sensor connected to the re-use blocking unit for detecting a temperature in the electrical therapy device and to output same to the re-use blocking triggering unit;
wherein the re-use blocking unit comprises a temperature evaluation means for triggering the blocking triggering unit if the temperature in the electrical therapy device which is outputted by the temperature sensor falls below a predetermined threshold value.

7. The electrical therapy device of claim 1, further comprising:
an energy supply unit adapted to supply the therapy device with the necessary energy, and
wherein the re-use blocking unit further comprises a triggering device adapted to disconnect the energy supply unit in dependence on the condition of the blocking triggering unit in order to interrupt the energy supply to the therapy device.

8. The electrical therapy device of claim 7 wherein the re-use blocking unit triggers the blocking triggering unit upon separation of the electrode line from the electrical therapy device.

9. The electrical therapy device of claim 7, wherein:
the re-use blocking unit triggers the blocking triggering unit upon separation of the electrode line from the electrical therapy device.

10. The electrical therapy device of claim 9, wherein:
the re-use blocking unit comprises an impedance measuring unit for determining an impedance of the electrode line and for triggering the blocking triggering unit if the measured impedance deviates from a predetermined value.

11. The electrical therapy device of claim 1, further comprising:
a means for controlling the functions of the therapy device,
wherein the re-use blocking unit instructs the control means to at least partially block electrical control of the therapy device during implantation in dependence on the condition of the blocking triggering unit.

12. The electrical therapy device of claim 11, wherein:
the re-use blocking unit comprises a first telemetric receiving unit that triggers the blocking triggering unit upon reception of a telemetric blocking signal.

13. The electrical therapy device of claim 11, wherein:
the re-use blocking unit comprises a first magnetically activatable receiving unit that triggers the blocking triggering unit upon magnetic activation thereof.

14. The electrical therapy device of claim 11, wherein:
the control means comprises a memory for a works operating program which is adapted to store a patient-specific works operating program for operation of the electrical therapy device and wherein the re-use blocking unit has an initialisation detection unit that triggers the blocking triggering unit upon initialisation of the stored works operating program.

15. The electrical therapy device of claim 11 wherein:
the re-use blocking unit comprises an impedance measuring unit for determining an impedance of said electrode line and for triggering the blocking triggering unit if the measured impedance deviates from a predetermined value.

16. The electrical therapy device of claim 11, wherein:
the re-use blocking unit comprises a detection unit for monitoring ECG signals of the heart and to trigger the blocking triggering unit when no more ECG signals are received in a predetermined period of time.

17. The electrical therapy device of claim 11, further comprising:
a temperature sensor connected to the re-use blocking unit for detecting a temperature in the electrical therapy device and to output same to the re-use blocking triggering unit;
wherein the re-use blocking unit comprises a temperature evaluation means for triggering the blocking triggering unit if the temperature in the electrical therapy device which is outputted by the temperature sensor falls below a predetermined threshold value.

18. The electrical therapy device of claim 11, further comprising:
a blocking deactivation means for overwriting the condition of the blocking triggering unit upon the reception of a blocking deactivation signal.

19. The electrical therapy device of claim 18, wherein:
the blocking deactivation means comprises a second telemetric receiving unit for telemetrically receiving the blocking deactivation signal.

20. The electrical therapy device of claim 19, wherein:
the blocking deactivation means comprises a means for decoding an ecoded password out of a received signal, and a means for verifying the received decoded password and to reset the blocking triggering unit when the received password is correct.

21. The electrical therapy device of claim 12, further comprising:
a blocking deactivation means for overwriting the condition of the blocking triggering unit upon the reception of a blocking deactivation signal.

22. The electrical therapy device of claim 21, wherein:
the blocking deactivation means comprises a second telemetric receiving unit for telemetrically receiving the blocking deactivation signal.

23. The electrical therapy device of claim 22, wherein:
the blocking deactivation means comprises a means for decoding an encoded password out of a received signal, and a means for verifying the received decoded password and to reset the blocking triggering unit when the received password is correct.

24. A packaging for an electrical therapy device as set forth in claim 13 wherein the packaging includes a magnet which is arranged in such a way as to magnetically activate the magnetically activatable receiving unit upon removal of the electrical therapy device from the packaging and thus to trigger the blocking triggering unit.

25. A combination of the electrical therapy device as set forth in claim 13 and a packaging wherein the packaging includes a magnet which is arranged in such a way as to magnetically activate the first magnetically activatable receiving unit upon removal of the electrical therapy device from the packaging and thus to trigger the blocking triggering unit.

26. The electrical therapy device of claim 13, further comprising:
blocking deactivation means for overwriting the condition of the blocking triggering unit upon the reception of a blocking deactivation signal.

27. The electrical therapy device of claim 26 wherein:
the blocking deactivation means comprises a second telemetric receiving unit for telemetrically receiving the blocking deactivation signal.

28. The electrical therapy device of claim 27, wherein:
the blocking deactivation means comprises a means for decoding an encoded password out of a received signal, and a means for verifying the received decoded password and to reset the blocking triggering unit when the received password is correct.

29. The electrical therapy device of claim 14, further comprising:
a blocking deactivation means for overwriting the condition of the blocking triggering unit upon the reception of a blocking deactivation signal.

30. The electrical therapy device of claim 29, wherein:
the blocking deactivation means comprises a second telemetric receiving unit for telemetrically receiving the blocking deactivation signal.

31. The electrical therapy device of claim 30, wherein:
the blocking deactivation means comprises a means for decoding an encoded password out of a received signal, and a means for verifying the received decoded password and to reset the blocking triggering unit when the received password is correct.

32. The electrical therapy device of claim 1, wherein:
the re-use blocking unit comprises a first telemetric receiving unit that triggers the blocking triggering unit upon reception of a telemetric blocking signal.

33. The electrical therapy device of claim 1, wherein:
the re-use blocking unit comprises a first magnetically activatable receiving unit that triggers the blocking triggering unit upon magnetic activation thereof.

34. The electrical therapy device of claim 1, wherein:
the re-use blocking unit comprises an impedance measuring unit for determining an impedance of the electrode line and for triggering the blocking triggering unit if the measured impedance deviates from a predetermined value.

35. The electrical therapy device of claim 1, wherein:
the re-use blocking unit comprises a detection unit for monitoring ECG signals of the heart and to trigger the blocking triggering unit when no more ECG signals are received in a predetermined period of time.

36. The electrical therapy device of claim 1, further comprising:
a temperature sensor connected to the re-use blocking unit for detecting a temperature in the electrical therapy device and to output same to the re-use blocking triggering unit;
wherein the re-use blocking unit comprises a temperature evaluation means for triggering the blocking triggering unit if the temperature in the electrical therapy device which is outputted by the temperature sensor falls below a predetermined threshold value.

* * * * *